United States Patent [19]

Carlos

[11] 4,186,077
[45] Jan. 29, 1980

[54] OXIDATION OF HYDROCARBON WAXES IN THE PRESENCE OF AMINE OXIDES

[75] Inventor: Donald D. Carlos, Grayson, Ky.

[73] Assignee: Ashland Oil, Inc., Ashland, Ky.

[21] Appl. No.: 2,087

[22] Filed: Jan. 9, 1979

Related U.S. Application Data

[63] Continuation-in-part of Ser. No. 918,131, Jun. 22, 1978.

[51] Int. Cl.$^2$ .......................... C07C 27/10; C09F 7/02
[52] U.S. Cl. ....................................... 208/3; 260/406; 260/451
[58] Field of Search ..................... 260/406, 451; 208/3

[56] References Cited

U.S. PATENT DOCUMENTS

| | | | |
|---|---|---|---|
| 2,338,634 | 1/1944 | Fuchs | 260/451 |
| 2,664,436 | 12/1953 | Heinrich | 208/3 X |
| 2,892,860 | 6/1959 | Pier | 260/451 |
| 3,803,137 | 4/1974 | Egan | 260/585 B |

*Primary Examiner*—John F. Niebling
*Attorney, Agent, or Firm*—Van D. Harrison, Jr.

[57] ABSTRACT

Hydrocarbon waxes are oxidized to high acid numbers by agitating the liquid hydrocarbon wax with an amine oxide while forcing gaseous air or oxygen through the liquid charge.

13 Claims, No Drawings

OXIDATION OF HYDROCARBON WAXES IN THE PRESENCE OF AMINE OXIDES

This application is a continuation-in-part of my co-pending application, Ser. No. 918,131, filed June 22, 1978.

NATURE OF THE INVENTION

This invention relates to the oxidation of hydrocarbon waxes. More particularly, it is concerned with a process for oxidizing hydrocarbon waxes to produce useful oxygenated products.

PRIOR ART

Oxidized petroleum fractions including waxes and petrolatums have, in the past, been employed as the source of saponifiable material in the production of lubricating greases and in the formulation of protective coatings. The oxidates employed for these purposes have been obtained by oxidizing selected petroleum fractions under controlled conditions such that the oxidation proceeds only to a limited extent.

Oxidation of petroleum fractions by the above described method had, associated with it, certain difficulties. Some petroleum fractions are not easily oxidized by the prior art processes and eventhough oxidizable, in some instances, require a preliminary induction period before the rate of oxidation becomes appreciable. Another problem associated wit oxidizing petrolatums is the discoloration of the final wax product rendering it aesthetically unattractive for use is some formulations.

OBJECT OF THE INVENTION

One object of this invention is to provide an improved process for the oxidation of petrolatums. Another object of the invention is to provide a process for oxidizing petrolatums more easily than has heretofore been possible.

SUMMARY OF THE INVENTION

Briefly stated, this invention comprises a process for oxidizing hydrocarbons comprising blowing through a molten mixture of hydrocarbon wax an oxidizing gas in the presence of a minor amount of a tertiary amine oxide or mixtures thereof.

The oxidation is conducted under suitable conditions of gas-flow, pressure and temperature to oxidize the hydrocarbon wax to a predetermined acid number.

DESCRIPTION OF THE INVENTION

The tertiary amine oxide used in the process of this invention may be represented by the general formula $R_1R_2R_3N \rightarrow O$ wherein $R_1$ is a higher alkyl radical having from 10 to 18 carbon atoms, such as dodecyl, decyl, hexadecyl, oleyl, stearyl, lauroyl, or an amide substituted group, such as

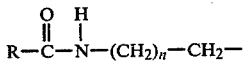

where RCO is a long chain alkanoyl radical of 10 to 18 carbon atoms and n is a small whole number between 1 and 5. $R_2$ and $R_3$ are a higher alkyl radical equivalent to $R_1$ or a lower alkyl radical of 1 to 9 carbon atoms such as methyl, ethyl, propyl, hydroxyethyl, hydroxyethoxyethyl, hydroxy polyethoxyethyl, etc. Examples of suitable tertiary amine oxides include lauroyl dimethyl amine oxide, coco dimethylamine oxide, dodecyl dimethyl amine oxide, didodecyl methyl amine oxide, tridodecyl amine oxide,

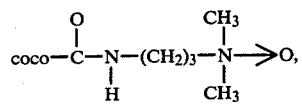

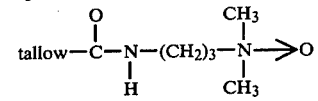

and the like. The tertiary nitrogen may also be in the form of a cyclic compound such as cocyl morpholine oxide, cocyl imidazoline oxide, etc. A preferred amine oxide is coco dimethylamine oxide. Ordinarily, the amine oxide is added in a concentration of amine oxide of between 0.2 and 2 parts by weight per 100 parts of hydrocarbon wax. Generally, the amine oxide will be in the form of an aqueous solution.

The hydrocarbons useful in this process are the conventional feedstocks previously used as oxidizer feedstock. Ordinarily, said feedstock comprises a mixture of saturated hydrocarbons having an average number of carbon atoms per molecule of 20 to 100. A particular characteristic of some feedstocks is the high concentration of nitrogen present in the molecular structure of some of the hydrocarbons making up the feedstock. The presence of nitrogen appears to inhibit the initiation of the oxidation of the hydrocarbons to their corresponding acids when blown with air.

Accordingly it may be desirable to add a promoting agent to overcome this initial inhibition of oxidation and to initiate the oxidation process.

I prefer to add as an oxidation promoter a quaternary ammonium compound having the formula:

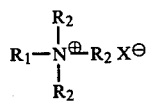

where $R_1$ is an aliphatic hydrocarbon radical of 10 or more carbon atoms, $R_2$ is an aliphatic hydrocarbon radical of 1-12 carbon atoms, and $X^\ominus$ is chloride, bromide, iodide, sulfate or bisulfate.

Although a number of quaternary compounds are deemed suitable for the promoter catalyst in the process of this invention, preferred promoters are dodecyltrimethylammonium chloride or a mixture of quaternary compounds having the formula:

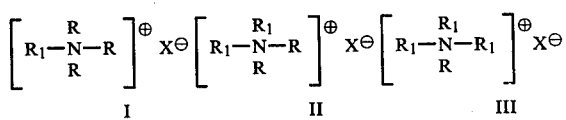

wherein R collectively represents the alkyl residue of a primary alcohol mixture composed of 30-70 wt. percent of (a) straight-chain $C_{16}$-$C_{22}$ alcohols and correspondingly from 70-30 wt. percent of (b) $C_8$-$C_{15}$Oxo alcohol consisting essentially of a mixture of straight-chain and single methyl branched isomers, said (a) and (b) being in relative proportions so that from about 95-80 wt. percent of said $R_1$ groups are straight-chain alkyl and correspondingly from 5-20 wt. percent are said branched alkyl, R is a $C_1$-$C_3$ alkyl group, X represents a chloride, bromide or iodide anion, and wherein said mixture of quaternaries is essentially composed of 0-10 wt. percent of compounds of Formula I, 60-85 wt. percent of compounds of Formula II, and 5-25 wt. percent of compounds of Formula III, said mixture being prepared by ammonolysis of a mixture of the corresponding $R_1OH$ alcohols and subsequent quaternization of the ammonolysis product.

The preparation and composition of these quaternary compounds is disclosed in U.S. Pat. No. 3,803,137 which is hereby incorporated by reference. The quaternary compound is added to the hydrocarbon fraction in a minor amount, preferably in a concentration of between 0.5 and 2 parts by weight per 100 parts of hydrocarbon.

Ordinarily, the process will be carried out as a batch process. Air or another oxidizing gas is forced through the reaction mixture of hydrocarbon, amine oxide and quaternary compound, if the latter is used, at a rate of between 0.5 and 10 liters (measured at 760 mm of mercury and 25° C.) per liter of hydrocarbon per minute at a temperature of between 150° and 180° C. Ordinarily, the temperature will rise as the oxidation proceeds so that only minimal heat may be required for the oxidation. The oxidation process is conducted at a pressure of between 50 and 400 psig (4.4–28.2 atmospheres). The process is discontinued when a desired acid number is reached. The term "acid number" is defined to mean the number of milligrams of potassium hydroxide required to neutralize 1 gram of sample.

The following example represents the best mode of conducting the process of this invention known to applicant at the date of filing this application.

EXAMPLE I

A number of air oxidations were conducted in laboratory tests using a 1 liter Parr bomb. In each test, the reactor charge amounted to approximately 500 cc of hydrocarbon. To the hydrocarbon material was added the weights of cocoamine oxide, (in a 50% solution in water) shown in the accompanying table. For comparison purposes runs were also made in which no cocoamine oxide was added. The feedstocks studied included both slack waxes and petrolatum samples. The reaction conditions were approximately three hours for each reaction at a temperature of approximately 320° F. (160° C.), a pressure of 200 psig (14.6 atmosphere), and an air input rate of 3.8 liters of air (measured at 25° C. and 1 atmosphere) per liter of reactor charge per minute. Acid number determinations were made at the end of each three-hour run. The results are shown in Table I. Table I also shows the acid numbers obtained when the same hydrocarbon materials were oxidized under the same conditions in the absence of amine oxide.

| BATCH AIR OXIDATION OF HYDROCARBONS WITH AND WITHOUT ADDITION OF AMINE OXIDE | | | |
|---|---|---|---|
| RUN NO. | HYDRO-CARBON TYPE | PARTS BY WT. OF COCO-AMINE OXIDE PER 100 PARTS HYDROCARBON | ACID NUMBER |
| 1-A | (1) | 0.25/99.75 | 50.0 |
| 1-B | (1) | 0/100 | 2.4 |
| 2-A | (2) | .25/99.75 | 48.9 |
| 2-B | (2) | 0/100 | 2.4 |
| 3-A | (3) | 0.5/99.5 | 34.1 |
| 3-B | (3) | 0/100 | 0.7 |

(1) Slack wax derived from a mixture of 250N Iranian Rostam and Louisiana sweet crude
(2) Slack wax derived from a mixture of 100N Iranian Rostam and Louisiana sweet crude
(3) Petrolatum From a comparison of Runs 1-A, 2-A and 3-A in which the amine oxide was added with Runs 1-B, 2-B and 3-B in which amine oxide was absent indicates that without the addition of the amine oxide no oxidation of the hydrocarbons would have resulted.

I claim:

1. A process for oxidizing liquid hydrocarbon comprising blowing an oxidizing gas through the liquid mass of said hydrocarbon in the presence of an amine oxide of the formula:

wherein $R_1$ is an alkyl radical having from 10 to 18 carbon atoms or an amide substituted group of the formula:

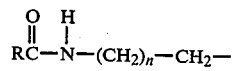

wherein RCO is a long chain alkanoyl radical and n is a small whole number; and $R_2$ and $R_3$ are selected from the group consisting of alkyl radicals equivalent to $R_1$, lower alkyl radicals of 1 to 9 carbon atoms, and hydroxyalkyl groups.

2. The process of claim 1 wherein $R_1$ of said amine oxide is an alkyl radical selected from the group consisting of dodecyl, decyl, hexadecyl, oleyl, stearyl and lauroyl and $R_2$ and $R_3$ are each alkyl radicals of 1 to 18 carbon atoms.

3. The process of claim 1 wherein said amine oxide is dodecyl dimethyl amine oxide.

4. The process of claim 1 wherein said amine oxide is didodecyl methyl amine oxide.

5. The process of claim 1 wherein said amine oxide is tridodecyl amine oxide.

6. The process of claim 1 wherein said amine oxide has the structural formula:

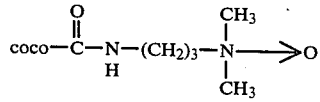

7. The process of claim 1 wherein said amine oxide has the structural formula:

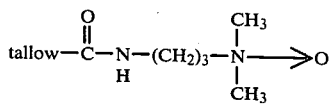

8. The process of claim 1 wherein the amount of amine oxide is between about 0.2 and about 2 parts by weight per 100 parts of liquid hydrocarbon.

9. The process of claim 1 wherein said liquid mass of hydrocarbon also contains as an oxidation promoter a quaternary ammonium compound having a formula:

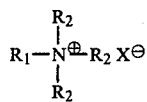

where $R_1$ is an aliphatic hydrocarbon radical of 10 or more carbon atoms, $R_2$ is an alipahtic hydrocarbon radical of 1 to 12 carbon atoms, and $X^\ominus$ is chloride, bromide, iodide, sulfate or bisulfate.

10. The process of claim 9 wherein said quaternary compound is selected from the group consisting of dodecyltrimethylammonium chloride and a mixture of quaternary compounds having the formula:

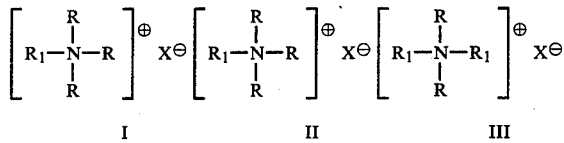

wherein R collectively represents the alkyl residue of a primary alcohol mixture composed of 30–70 wt. percent of (a) straight-chain $C_{16}$–$C_{22}$ alcohols and correspondingly from 70–30 wt. percent of (b) $C_8$–$C_{15}$ Oxo alcohols consisting essentially of a mixture of straight-chain and single methyl branched isomers, said (a) and (b) being in relative proportions so that from about 95–80 wt. percent of said R groups are straight-chain alkyl and correspondingly from 5–20 wt. percent are said branched alkyl, R is a $C_1$–$C_3$ alkyl group, X represents a chloride, bromide or iodide anion, and wherein said mixture of quaternaries is essentially composed of 0–10 percent of compounds of Formula I, 60–85 wt. percent of compounds of Formula II, and 5–25 wt. percent of compounds of Formula III, said mixture being prepared by ammonolysis of a mixture of the corresponding $R_1OH$ alcohols and subsequent quaternization fo the ammonolysis product.

11. The process of claim 9 wherein said quaternary ammonium compound is present in a concentration of between about 0.5 and about 2 parts by weight per 100 parts of liquid hydrocarbon.

12. The process of claim 1 wherein said liquid hydrocarbon wax or petrolatum has an average of between about 20 and about 100 carbon atoms per molecule, said amine oxide is cocoamine oxide present in an amount of between about 0.2 and about 2 parts by weight of liquid hydrocarbon wax or petrolatum, said oxidizing gas is forced through said liquid wax or petrolatum at a rate of between 0.5 and 10 liters (measured at 760 mm of mercury and 25° C.) of gas per liter of hydrocarbon per minute at a temperature of between about 150° and 180° C.

13. The process of claim 12 wherein said liquid hydrocarbon wax or petrolatum also contains between about 0.5 and 2 parts by weight of a quaternary ammonium compound.

* * * * *